(12) United States Patent
Liu

(10) Patent No.: US 11,986,679 B2
(45) Date of Patent: May 21, 2024

(54) NEUTRON CAPTURE THERAPY SYSTEM

(71) Applicant: Neuboron Therapy System Ltd., Fujian (CN)

(72) Inventor: Yuan-Hao Liu, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 864 days.

(21) Appl. No.: 17/089,066

(22) Filed: Nov. 4, 2020

(65) Prior Publication Data

US 2021/0069528 A1 Mar. 11, 2021

Related U.S. Application Data

(63) Continuation of application No. PCT/CN2019/086063, filed on May 8, 2019.

(30) Foreign Application Priority Data

May 18, 2018 (CN) .......................... 201810479382.9

(51) Int. Cl.
*A61N 5/10* (2006.01)
*A61B 6/04* (2006.01)
(Continued)

(52) U.S. Cl.
CPC .......... *A61N 5/1077* (2013.01); *A61B 6/0407* (2013.01); *G21F 7/06* (2013.01);
(Continued)

(58) Field of Classification Search
CPC ...... A61N 2005/109; A61N 2005/1094; A61B 6/0407
See application file for complete search history.

(56) References Cited

U.S. PATENT DOCUMENTS

2007/0055090 A1* 3/2007 Neustadter ........... A61N 5/1049
600/3
2008/0234865 A1 9/2008 Sommer
(Continued)

FOREIGN PATENT DOCUMENTS

CN 103052425 A 4/2013
CN 105435376 A 3/2016
(Continued)

OTHER PUBLICATIONS

International Search Report of PCT/CN2019/086063, dated Jul. 30, 2019.

*Primary Examiner* — Thaddeus B Cox
(74) *Attorney, Agent, or Firm* — Locke Lord LLP; Tim Tingkang Xia, Esq.

(57) ABSTRACT

A neutron capture therapy system includes a neutron generation device for generating a neutron beam, an irradiation room for irradiating an irradiated body with the neutron beam and a placement table that is accommodated in the irradiation room and is adapted to support the irradiated body. The placement table includes a placement member for supporting a patient, an adjustment device for adjusting a spatial position of the placement member, a driving rod connected between the adjustment device and the placement member and a first shielding member covering the adjustment device. The first shielding member prevents the adjustment device from being radiated by radioactive rays. The adjustment device is disposed in the first shielding member that is basically sealed, thereby greatly reducing radiation damage to the adjustment device by neutrons and gamma rays and prolonging the service life of the adjustment device.

20 Claims, 3 Drawing Sheets

(51) Int. Cl.
*G21F 7/06* (2006.01)
*G21G 4/02* (2006.01)
*G21K 1/10* (2006.01)

(52) U.S. Cl.
CPC ............... *G21G 4/02* (2013.01); *G21K 1/10* (2013.01); *A61N 2005/109* (2013.01); *A61N 2005/1094* (2013.01)

(56) References Cited

U.S. PATENT DOCUMENTS

| | | | |
|---|---|---|---|
| 2014/0171725 A1* | 6/2014 | Adler | G21F 3/00 600/1 |
| 2018/0249972 A1* | 9/2018 | Yifat | A61N 5/1081 |

FOREIGN PATENT DOCUMENTS

| | | | |
|---|---|---|---|
| CN | 105536152 A | 5/2016 | |
| CN | 106474635 A | 3/2017 | |
| CN | 107007947 A | 8/2017 | |
| CN | 206867514 U | 1/2018 | |
| EP | 2612692 A1 | 7/2013 | |
| EP | 3136400 A1 | 3/2017 | |
| JP | 2017009393 A | 1/2017 | |
| WO | 2017170909 A1 | 10/2017 | |
| WO | 2018056146 A1 | 3/2018 | |
| WO | 2018086367 A1 | 5/2018 | |
| WO | WO-2019050551 A1 * | 3/2019 | ............ A61B 6/022 |

* cited by examiner

NEUTRON CAPTURE THERAPY SYSTEM

RELATED APPLICATION INFORMATION

This application is a continuation of International Application No. PCT/CN2019/086063, filed on May 8, 2019, which claims priority to Chinese Patent Application No. 201810479382.9, filed on May 18, 2018, the disclosures of which are hereby incorporated by reference.

FIELD OF THE DISCLOSURE

The present disclosure relates to a radioactive irradiation system, and more particularly to a neutron capture therapy system.

BACKGROUND OF THE DISCLOSURE

As atomics moves ahead, radiotherapy such as Cobalt-60 therapy, linear accelerator therapy and electron beam therapy has been one of the major approaches to cancer treatment. However, conventional photon or electron therapy has undergone physical restrictions of radioactive rays. For example, a large amount of normal tissue on a beam path is damaged as tumor cells are killed. Moreover, tumor cells have different radiosensitivities, and as a result conventional radiotherapy falls short of treatment effectiveness on radioresistant malignant tumors (such as glioblastoma multiforme and melanoma).

For the purpose of reducing radiation damage to the normal tissue surrounding a tumor site, target therapy in chemotherapy has been employed in the radiotherapy. While for high-radioresistant tumor cells, radiation sources with high RBE (relative biological effectiveness) including such as proton, heavy particle and neutron capture therapy have also developed. Among them, the neutron capture therapy combines the target therapy with the RBE, such as the boron neutron capture therapy (BNCT). By virtue of specific grouping of boronated pharmaceuticals in the tumor cells and precise neutron beam regulation, BNCT is provided as a better cancer therapy choice than conventional radiotherapy.

A neutron capture therapy system includes a neutron beam generator, a neutron beam moderating device, a collimator, an irradiation room, a preparation room and a placement table for supporting a patient. Generally, the moderating device is buried in a wall of the irradiation room, and the collimator is fixedly disposed at a front end of the moderating device or on the placement table. Before irradiation, a spatial position of a placement member for supporting a patient on the placement table needs to be adjusted to enable a body part to be irradiated of the patient to be aligned with the collimator and the neutron beam generator. To ensure strength, an adjustment device for adjusting the spatial position of the placement member is generally made of metal. In a process of implementing neutron beam irradiation on the patient, the adjustment device is always exposed to radioactive rays having a relatively high radiation dose of neutron beams, y rays, and the like, so that the adjustment device tends to be activated, and as a result the service life of the placement table is terminated prematurely.

The statements in this section merely provide background information related to the present disclosure and may not constitute prior art.

SUMMARY

To resolve the above problems, an aspect of the disclosure provides a neutron capture therapy system, provided with a neutron generation device for generating a neutron beam, an irradiation room for irradiating an irradiated body with the neutron beam and a placement table that is accommodated in the irradiation room and is adapted for supporting the irradiated body. The neutron generation device includes a neutron beam generator for generating the neutron beam, a moderator for slowing down the neutron beam to an epithermal neutron energy range and a reflector for guiding deflected neutrons back to the moderator. The placement table includes a placement member for supporting a patient, an adjustment device for adjusting a spatial position of the placement member, a driving rod connected between the adjustment device and the placement member and a first shielding member covering the adjustment device. The first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

Implementations of this aspect may include one or more of the following features.

Further, the neutron generation device further includes a thermal neutron absorber for absorbing thermal neutrons to protect superficial normal tissue from an overdose during treatment and a radiation shielding for shielding against leaked neutrons and photons to reduce a dose to normal tissue in a non-irradiation area.

Further, the placement table further includes a second shielding member located between the through slot on the first shielding member and the adjustment device, the driving rod drives the second shielding member to move in the through slot, and the second shielding member prevents the adjustment device from being irradiated by the radioactive rays.

Preferably, the first shielding member is a hollow sphere or a hollow polyhedron, the first shielding member has a body portion, the through slot is provided in a side, adjacent to the placement member, of the body portion, and the driving rod passes through the through slot to be sequentially connected to the second shielding member and the adjustment device.

Preferably, when the driving rod drives the second shielding member to move to an optional position of the through slot, a border of a projection of the through slot on a plane parallel to the ground is located in a border of a projection of the second shielding member on the plane parallel to the ground.

Another aspect of the disclosure provides a neutron capture therapy system including a placement member for supporting a patient, an adjustment device for adjusting a spatial position of the placement member, a driving rod connected between the adjustment device and the placement member and a first shielding member covering the adjustment device. The first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

Implementations of this aspect may include one or more of the following features.

Preferably, the first shielding member is a hollow sphere or a hollow polyhedron.

Further, the first shielding member has a body portion, the through slot is provided in a side, adjacent to the placement member, of the body portion, and the driving rod passes through the through slot to be connected to the adjustment device.

Further, the neutron capture therapy system further includes a second shielding member located between the through slot on the first shielding member and the adjustment device.

Preferably, the second shielding member is arc-shaped or flat plate-shaped.

Preferably, when the driving rod drives the second shielding member to move to an optional position, a border of a projection of the through slot on a plane parallel to the ground is located in a border of a projection of the second shielding member on the plane parallel to the ground.

In yet another aspect of the disclosure, a neutron capture therapy system is provided for reducing radiation damage to an adjustment device by neutrons and gamma rays and prolonging the service life of the adjustment device. The neutron capture therapy system includes: an irradiation room for irradiating an irradiated body with a neutron beam, a placement member for supporting the irradiated body, wherein the placement member is accommodated in the irradiation room, an adjustment device for adjusting a spatial position of the placement member, a driving rod connected between the adjustment device and the placement member, anda first shielding member covering the adjustment device, wherein the first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

Implementations of this aspect may include one or more of the following features.

Furthermore, the neutron capture therapy system includes a neutron generation device for generating a neutron beam.

Preferably, the neutron generation device includes a neutron beam generator for generating the neutron beam, a moderator for slowing down the neutron beam to an epithermal neutron energy range, and a reflector for guiding deflected neutrons back to the moderator.

Furthermore, the first shielding member has a body portion, the through slot is provided in a side, adjacent to the placement member, of the body portion, and the driving rod passes through the through slot to be connected to the adjustment device.

Furthermore, the neutron capture therapy system includes a second shielding member located between the through slot on the first shielding member and the adjustment device.

Compared with the prior art, the technical solutions of the embodiments have the following beneficial effects: the adjustment device is disposed in the first shielding member that is basically sealed, thereby greatly reducing radiation damage to the adjustment device by neutrons and gamma rays and prolonging the service life of the adjustment device.

Further areas of applicability will become apparent from the description provided herein. It should be understood that the description and specific examples are intended for purposes of illustration only and are not intended to limit the scope of the present disclosure.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

The following description of the preferred embodiment(s) is merely exemplary in nature and is in no way intended to limit the invention, its application, or uses.

The application of a neutron capture therapy as an effective treatment for cancer has been increasing gradually in recent years, and a BNCT is the most common. Neutrons for the BNCT may be supplied by a nuclear reactor or an accelerator. An accelerator-based BNCT is used as an example in embodiments of the disclosure.

The following describes implementations of the present disclosure in detail with reference to the accompanying drawings. In addition, in the description below, the same or equivalent elements are marked with a same symbol, and repeated descriptions are omitted. Moreover, an xyz coordinate system (with reference to FIG. 2) is set, where an irradiation direction of a following neutron beam N is set as an X-axis, a direction orthogonal to the irradiation direction of the neutron beam N is set as a Y-axis, and a direction perpendicular to the ground is set as a Z-axis. A plane formed by the X-axis and the Y-axis is defined as a first plane, and the first plane is parallel to the ground. The X-axis, Y-axis and Z-axis are used in descriptions of position relationships between the constituents.

The terms related to space such as "up", "down", "left", "right" "front", and "rear" can be used for simplifying the descriptions of the relationships between one component and another component. As shown in the figures, a longitudinal direction is parallel to the Y-axis, a vertical direction is parallel to the Z-axis, and a transverse direction is parallel to the X-axis.

Figure 1:
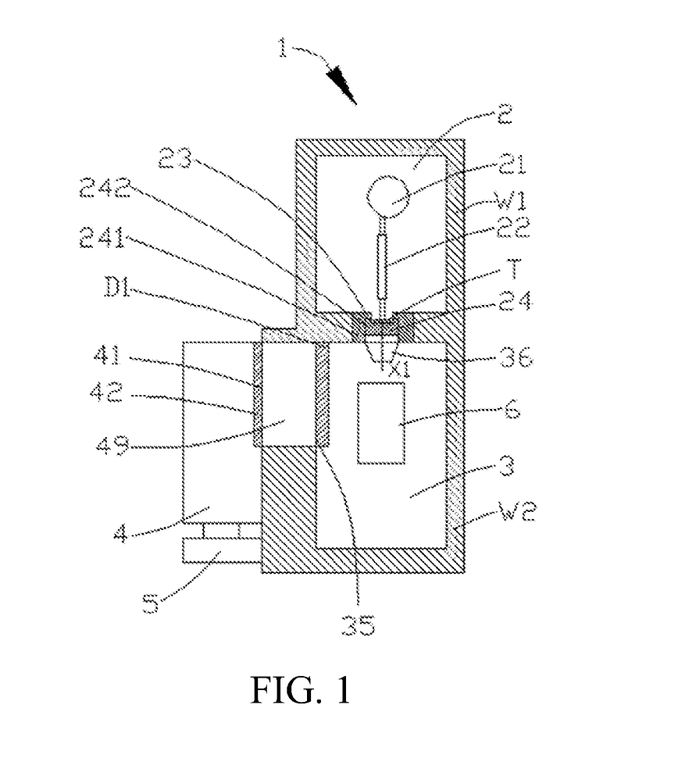
FIG. 1 is a top view of a neutron capture therapy system according to the disclosure.

As shown in FIG. 1, a neutron capture therapy system 1 includes a neutron generation device 2 for generating a therapeutic neutron beam N, an irradiation room 3 for irradiating an irradiated body, for example, a patient, with the neutron beam N, a preparation room 4 for performing preparation work before irradiation, a management room 5 for implementing irradiation control and a placement table 6 for supporting the patient to enter or leave the irradiation room 3.

The neutron generation device 2 is constructed to generate the neutron beam N outside the irradiation room 3 and irradiate the patient with the neutron beam N. The neutron generation device 2 includes a cyclotron 21 for accelerating a charged particle beam, a neutron beam generator 23 reacting with the charged particle beam to generate the neutron beam N and a charged particle beam transmission portion 22 for transmitting the charged particle beam and located between the cyclotron 21 and the neutron beam generator 23. The neutron generation device 2 is surrounded by a shielding wall W1 made of concrete. The charged particle beam transmission portion 22 transmits the charged particle beam to the neutron beam generator 23. One end of the transmission portion is connected to the cyclotron 21, and the other end is connected to the neutron beam generator 23. In other embodiments, other accelerators may be used in place of the cyclotron. According to actual requirements, beam control devices such as a beam adjustment portion, a current monitor and a charged particle scanning portion may be disposed on the charged particle beam transmission portion 22. The beam adjustment portion controls the travel direction and the beam diameter of the charged particle beam. The current monitor measures a current value (that is, an electric charge and an irradiation dose rate) of the charged particle beam in real time. The charged particle beam scanning portion scans the charged particle beam and controls a position at which the charged particle beam irradiates the neutron beam generator 23. The neutron beam generator 23 includes a target T reacting with the charged particle beam to generate the neutron beam N and a beam shaping assembly 24 decelerating and shielding against the generated neutron beam N. The neutron beam N generated from the neutron beam generator 23 includes a fast neutron beam, an epithermal neutron beam, a thermal neutron beam and gamma rays. An epithermal neutron energy range is between 0.5 eV and 40 keV, a thermal neutron energy range is less than 0.5 eV, and a fast neutron energy range is more than 40 keV. Specifically, the beam shaping assembly 24 includes a moderator 241 for slowing down the neutron beam N generated from the target T to the epithermal neutron energy range, a reflector 242 for guiding deflected neutrons back to the moderator 241 to increase the intensity of the epithermal neutron beam, a thermal neutron absorber assembly for absorbing thermal neutrons to protect superficial normal tissue from an overdose during treatment and a radiation shielding assembly for shielding against leaked neutrons and photons to reduce a dose to normal tissue in a non-irradiation area. In an exemplary embodiment, the target T is made of lithium and is usually a lithium (Li) target and a beryllium (Be) target. The charged particle beam is accelerated to have sufficient energy to overcome a nuclear Coulomb repulsive force of the target T, and the $^{7}Li(p,n)^{7}Be$ nuclear reaction with the target T takes place to generate the neutron beam. The nuclear reaction between the epithermal neutron beam and boron that enters a tumor inside the body of the patient mainly produces the treatment effect. The target T is disposed outside the shielding wall W1, and the beam shaping assembly 24 is buried in the shielding wall W1 in the travel direction of the neutron beam N.

Still referring to FIG. 1, the irradiation room 3 includes a shielding wall W2, an entrance/exit 35 provided in the shielding wall W2 to allow the passage of a patient and a shielding door D1 opening and closing the entrance/exit 35. A patient is placed in the irradiation room 3 to receive the irradiation of the neutron beam N for treatment. A conical collimator 36 for emitting the neutron beam N is disposed on the shielding wall W2 close to the neutron generation device 2. The neutron beam N is emitted from the collimator 36 and defines a neutron beam axis X1. In other embodiments, the collimator 36 may be disposed with another shape such as a cylindrical shape and a cuboid shape. The preparation room 4 is arranged for implementing the required preparation work before a patient S is irradiated with the neutron beam N. The preparation work includes fixing the patient on the placement table 6, positioning the patient, making three-dimensional positioning marks, and the like. In this embodiment of the disclosure, the preparation room 4 is disposed on the left side of the irradiation room 3. In other embodiments, the preparation room 4 may be disposed at an optional position around the irradiation room 3. The preparation room 4 is provided with an entrance/exit 41 for a patient to enter or leave the irradiation room 3 and a door 42 for opening or closing the entrance/exit 41. A passage 49 is provided between the entrance/exit 41 of the preparation room 4 and the entrance/exit 35 of the irradiation room 3 for the patient to enter the irradiation room 3 from the preparation room 4. A guide rail (not shown) for moving the placement table is disposed in the preparation room 4, the irradiation room 3 and the passage 49.

The management room 5 is arranged for managing an entire procedure implemented by using the neutron capture therapy system 1. For example, a manager confirms the status of the preparation work in the preparation room 4 with eyes from the inside of the management room 5, and the manager operates a control device to control the start and stop of the irradiation of the neutron beam N.

Figure 2:
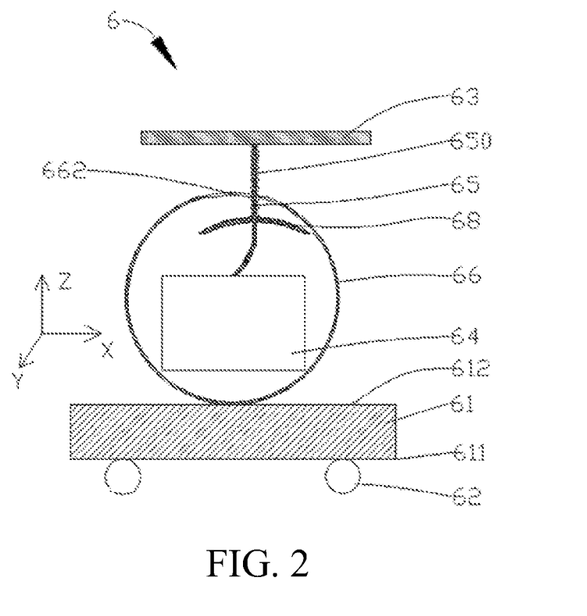
FIG. 2 is a sectional view of a placement table of Embodiment 1 of a neutron capture therapy system according to the disclosure, wherein a driving rod is located at a first end point of a through slot.

Referring to FIG. 2, the placement table 6 includes: a base portion 61, a driving portion 62 for moving the base portion 61 on the ground, a placement member 63 for supporting the patient, an adjustment device 64 for adjusting a spatial position of the placement member 63, a driving rod 65 connected between the adjustment device 64 and the placement member 63, a first shielding member 66 covering the adjustment device 64 and a second shielding member 68 located in the first shielding member 66.

The base portion 61 is arranged for supporting the first shielding member 66, the second shielding member 68, the adjustment device 64, the driving rod 65 and the placement member 63, and has a lower surface 611 facing the ground and an upper surface 612 opposite to the lower surface. In the disclosure, the entire base portion 61 has a cuboid shape. In other implementations, the base portion 61 may be disposed having a cylindrical shape or other shapes. The driving portion 62 is mounted on the lower surface 611. The driving portion 62 supports the base portion 61, the first shielding member 66, the second shielding member 68, the adjustment device 64, the driving rod 65 and the placement member 63, and moves on the ground according to a predetermined track. Preferably, the driving portion 62 is four wheels, these wheels may give the driving portion 62 a driving force to move on the ground by manpower or a motor. In the disclosure, the placement table 6 moves along the guide rail in the irradiation room 3 and the preparation room 4. In other embodiments, the base portion 61 may be omitted, and the driving portion 62 is disposed on the first shielding member 66.

The placement member 63 is arranged for supporting a patient, and may be flat plate-shaped, or may be chair-shaped or has other shapes suitable for supporting a patient.

One end of the driving rod 65 is fixedly connected to the placement member 63, and the other end is connected to the adjustment device 64. In the disclosure, the adjustment device 64 may be any one of common driving mechanisms, for example, a connecting rod mechanism and a gear mechanism, or a combination of a plurality of driving mechanisms, which can drive the driving rod 65 to move in the directions of the X-axis, the Y-axis and the Z-axis and can drive the driving rod 65 to rotate around the X-axis, the Y-axis and the Z-axis. The adjustment device 64 may be manpower-driven, power-driven or air-operated. The adjustment device 64 is mainly made of metal. The first shielding member 66 and the second shielding member 68 cover the adjustment device 64 to prevent the adjustment device 64 from being activated. The first shielding member 66 and the second shielding member 68 are made of one or more of materials such as lead, boron, titanium powder, aluminum powder and boron carbide that can shield against neutrons and gamma rays.

The driving rod 65 is a telescopic rod, and the position of the placement member 63 in the direction of the Z-axis may be adjusted by using the telescopic driving rod 65. Certainly, the driving rod 65 may also not be a telescopic rod, and only the adjustment device 64 is adapted to adjust the position of the placement member 63 in the direction of the Z-axis. A shielding film is coated on the outer surface of the driving rod 65, or a shielding cover 650 is mounted on the outer surface of the driving rod 65, to prevent the driving rod 65 from radiation of neutrons and gamma rays. The shielding cover 650 may be a telescopic thread cover. It should be noted that the driving rod 65 is only a linkage member between the placement member 63 and the adjustment device 64, and may be an output end of the adjustment device 64, or may be an additionally provided rod independent of the adjustment device 64.

Figure 3:
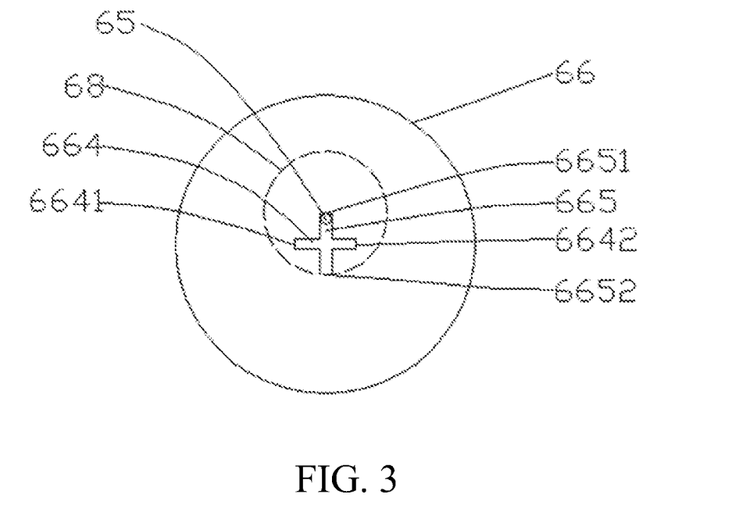
FIG. 3 is a top view of a placement table without a base portion, a placement member, a driving portion and an adjustment device of Embodiment 1 of a neutron capture therapy system according to the disclosure, wherein a driving rod is located at a third end point of a through slot.

Referring to FIG. 2 and FIG. 3, specifically, the first shielding member 66 is supported on the upper surface 612 of the base portion 61, and includes a spherical body portion 660 and a through slot 662 that is provided in a side, adjacent to the placement member 63, of the body portion 660 and provides a receiving space for the driving rod 65 to move. The adjustment device 64 is disposed in the body portion 660 of the first shielding member 66. The driving rod 65 passes downward through the through slot 662 to be sequentially fixedly connected to the second shielding member 68 and the adjustment device 64. The connection manner may be any one of common connection manners such as a threaded connection, a bolt connection or a fastener connection. The body portion 660 is a hollow sphere. The through slot 662 is a through slot penetrating the upper half part of the body portion 660 in the direction of the Z-axis. In this embodiment, the through slot 662 is slots that intersect and penetrate, and includes a first through slot 664 parallel to the X-axis and a second through slot 665 parallel to the Y-axis. The first through slot 664 and the second through slot 665 intersect and penetrate, and have projections of the first through slot 664 and the second through slot 665 on the first plane have a cross shape. A first size is defined as the maximum size of the through slot 662 in the direction parallel to the X-axis, and a second size is defined as the maximum size of the through slot 662 in the direction parallel to the Y-axis. The values of the first size and the second size are determined according to an actual use requirement, and may be equal or not equal. In other embodiments, the through slot 662 may be an entire circular slot, an entire square slot or an irregular-shaped slot. The through slot 662 includes a first end point 6641 located at the leftmost end, a second end point 6642 located at the rightmost end, a third end point 6651 located at the rearmost end and a fourth end point 6652 located at the frontmost end. Only the through slot 662 for the driving rod 65 to move is provided in the first shielding member 66, and is basically a sealed space. As a result, the adjustment device 64 disposed in the first shielding member 66 receives very little radiation of neutrons and gamma rays, thereby minimizing the speed at which the adjustment device 64 is activated. When being driven by the adjustment device 64, the driving rod 65 drives the placement member 63 to move in the through slot 662, so that the position of the placement member 63 can be adjusted freely in the directions of the X-axis, the Y-axis and the Z-axis. Moreover, the adjustment device 64 may further drive the driving rod 65 to drive the placement member 63 to rotate around the X-axis, the Y-axis and the Z-axis. In other embodiments, the first shielding member 66 may be disposed as a hollow polyhedron such as a hollow cuboid, a hollow cube and a hollow prism. All shapes that can accommodate the adjustment device 64 and can fit the second shielding member 68 to achieve an adequate shielding effect are feasible. It is easy to be understood that the first shielding member 66 can be opened or closed to facilitate the mounting of the adjustment device 64 in the first shielding member 66.

Referring to FIG. 2 and FIG. 3, in the direction of the Z-axis, the second shielding member 68 is located between the through slot 662 of the first shielding member 66 and the adjustment device 64. The second shielding member 68 is arranged for shielding against a small amount of neutrons and gamma rays entering the first shielding member 66 from the through slot 662 of the first shielding member 66. In Embodiment 1, the second shielding member 68 is an arc-shaped thin plate, and the projection of the second shielding member 68 on the first plane is circular. To ensure that the second shielding member 68 can maximally shield against a small amount of neutrons and gamma rays entering the first shielding member 66 from the through slot 662 of the first shielding member 66, when the driving rod 65 drives the second shielding member 68 to move to an optional position, a border of a projection of the through slot 662 on the first plane is located in a border of a projection of the second shielding member 68 on the first plane.

Figure 4:
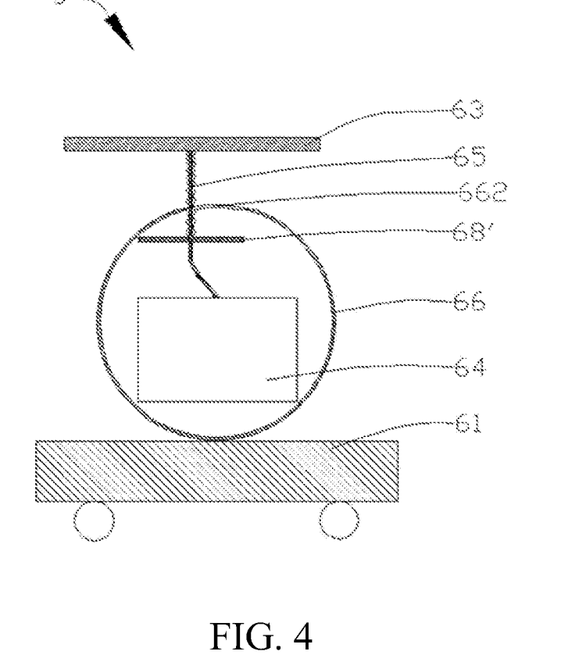
FIG. 4 is a sectional view of a placement table of Embodiment 2 of a neutron capture therapy system according to the disclosure, wherein a driving rod is located at a second end point of a through slot.
Figure 5:
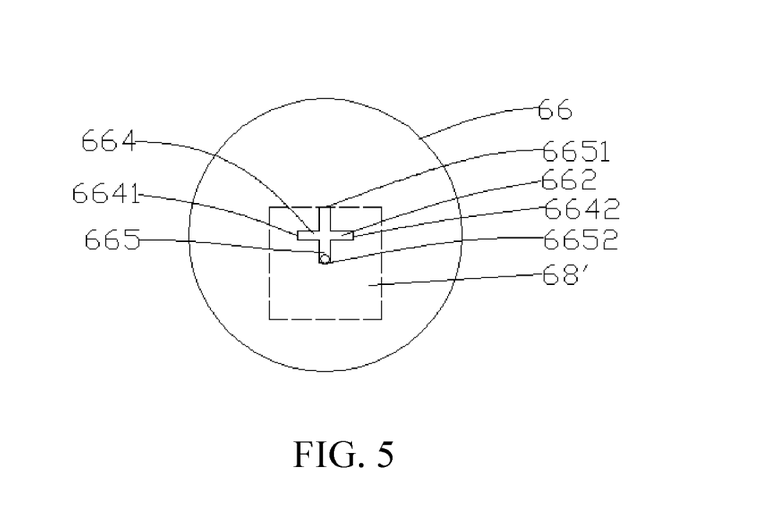
FIG. 5 is a top view of a placement table without a base portion, a placement member, a driving portion and an adjustment device of Embodiment 2 of a neutron capture therapy system according to the disclosure, wherein a driving rod is located at a fourth end point of a through slot.

Referring to FIG. 4 and FIG. 5, in Embodiment 2, a second shielding member 68' is flat plate-shaped, and a projection of the second shielding member 68' on the first plane is square. To ensure that the second shielding member 68' can maximally shield against a small amount of neutrons and gamma rays entering the first shielding member 66 from the through slot 662 of the first shielding member 66, when the driving rod 65 drives the second shielding member 68' to move to an optional position, a border of a projection of the through slot 662 on the first plane is located in a border of a projection of the second shielding member 68' on the first plane. Further, the flat plate-shaped second shielding member 68' may be an elastic plate or a telescopic plate, so that edges of the second shielding member 68 and 68' are as close as possible to the first shielding member 66. Certainly, the second shielding members 68 and 68' are not limited to these two shapes, and any other shape that can be conveniently manufactured and mounted and can achieve an adequate shielding effect is feasible. A difference between Embodiment 2 and Embodiment 1 only lies in that the second shielding members 68 and 68' have different shapes. Therefore, other components are not described herein again.

The adjustment device 64 is disposed in the first shielding member 66 that is basically sealed, thereby greatly reducing radiation damage to the adjustment device 64 by neutrons and gamma rays. Moreover, the second shielding member 68 further shields against a small amount of neutrons and gamma rays entering from the through slot 662 of the first shielding member 66, so that the amount of radiation received by the adjustment device 64 can be basically ignored, thereby greatly prolonging the service life of the adjustment device 64.

The neutron capture therapy system and the placement table disclosed in the disclosure are not limited to the content in the foregoing embodiments and the structures represented by the drawings. For example, the moderator may be disposed as a cylinder, a plurality of cooling devices may be disposed, and correspondingly a plurality of accommodating pipes may be provided. Based on the disclosure, obvious changes, replacements or modifications to the materials, shapes and positions of the components all fall within the protection scope of the disclosure.

What is claimed is:

1. A neutron capture therapy system comprising:
   a neutron generation device for generating a neutron beam, including:
   a neutron beam generator for generating the neutron beam,
   a moderator for slowing down the neutron beam to an epithermal neutron energy range, and
   a reflector for guiding deflected neutrons back to the moderator,
   an irradiation room for irradiating an irradiated body with the neutron beam, and
   a placement table for supporting the irradiated body, wherein the placement table is accommodated in the irradiation room,
   wherein the placement table comprises:
   a placement member for supporting a patient,
   an adjustment device for adjusting a spatial position of the placement member,
   a driving rod connected between the adjustment device and the placement member, and
   a first shielding member covering the adjustment device, wherein the first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

2. The neutron capture therapy system according to claim 1, wherein the placement table further comprises a second shielding member located between the through slot on the first shielding member and the adjustment device, the driving rod drives the second shielding member to move in the through slot, and the second shielding member prevents the adjustment device from being irradiated by the radioactive rays.

3. The neutron capture therapy system according to claim 2, wherein the second shielding member is arc-shaped or flat plate-shaped.

4. The neutron capture therapy system according to claim 2, wherein the first shielding member is a hollow sphere or a hollow polyhedron, the first shielding member has a body portion, the through slot is provided in a side, adjacent to the placement member, of the body portion, and the driving rod passes through the through slot to be sequentially connected to the second shielding member and the adjustment device.

5. The neutron capture therapy system according to claim 2, wherein when the driving rod drives the second shielding member to move to an optional position of the through slot, a border of a projection of the through slot on a plane parallel to a ground is located in a border of a projection of the second shielding member on the plane parallel to the ground.

6. The neutron capture therapy system according to claim 1, wherein a shielding film is coated on an outer surface of the driving rod.

7. The neutron capture therapy system according to claim 1, wherein a shielding cover is mounted on an outer surface of the driving rod.

8. A neutron capture therapy system comprising:
   a placement member for supporting a patient,
   an adjustment device for adjusting a spatial position of the placement member,
   a driving rod connected between the adjustment device and the placement member, and
   a first shielding member covering the adjustment device, wherein the first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

9. The neutron capture therapy system according to claim 8, wherein the first shielding member is a hollow sphere or a hollow polyhedron.

10. The neutron capture therapy system according to claim 8, wherein the first shielding member has a body portion, the through slot is provided in a side, adjacent to the placement member, of the body portion, and the driving rod passes through the through slot to be connected to the adjustment device.

11. The neutron capture therapy system according to claim 8, further comprising a second shielding member located between the through slot on the first shielding member and the adjustment device.

12. The neutron capture therapy system according to claim 11, wherein the second shielding member is arc-shaped or flat plate-shaped.

13. The neutron capture therapy system according to claim 11, wherein when the driving rod drives the second shielding member to move to an optional position, a border of a projection of the through slot on a plane parallel to a ground is located in a border of a projection of the second shielding member on the plane parallel to the ground.

14. The neutron capture therapy system according to claim 8, wherein a shielding film is coated on an outer surface of the driving rod.

15. The neutron capture therapy system according to claim 8, wherein a shielding cover is mounted on an outer surface of the driving rod.

16. A neutron capture therapy system comprising:
   an irradiation room for irradiating an irradiated body with a neutron beam,
   a placement member for supporting the irradiated body, wherein the placement member is accommodated in the irradiation room,
   an adjustment device for adjusting a spatial position of the placement member,
   a driving rod connected between the adjustment device and the placement member, and
   a first shielding member covering the adjustment device, wherein the first shielding member prevents the adjustment device from being irradiated by radioactive rays, the adjustment device drives the driving rod to move to adjust the spatial position of the placement member, and the first shielding member is provided with a through slot providing a receiving space for the driving rod to move.

17. The neutron capture therapy system according to claim 16, further including a neutron generation device for generating a neutron beam.

18. The neutron capture therapy system according to claim 17, wherein the neutron generation device comprises a neutron beam generator for generating the neutron beam, a moderator for slowing down the neutron beam to an epithermal neutron energy range, and a reflector for guiding deflected neutrons back to the moderator.

19. The neutron capture therapy system according to claim 16, wherein the first shielding member has a body portion, the through slot is provided in a side, adjacent to the placement member, of the body portion, and the driving rod passes through the through slot to be connected to the adjustment device.

20. The neutron capture therapy system according to claim 16, further including a second shielding member located between the through slot on the first shielding member and the adjustment device.

* * * * *